United States Patent [19]

Sato et al.

[11] 4,070,254

[45] Jan. 24, 1978

[54] PROCESS FOR PREPARING A PURIFIED METHACRYLIC ACID ESTER

[75] Inventors: Ryoji Sato, Kosugi; Takanori Musha, Takaoka, both of Japan

[73] Assignee: Nippon Zeon Co., Ltd., Tokyo, Japan

[21] Appl. No.: 693,444

[22] Filed: June 7, 1976

[30] Foreign Application Priority Data

June 10, 1975    Japan ................................ 50-70005

[51] Int. Cl.$^2$ .......................... B01D 3/36; C07C 69/52
[52] U.S. Cl. ....................................... 203/83; 203/45; 203/82; 203/95; 560/218
[58] Field of Search ....................... 203/83, 82, 76, 75, 203/39, 45, 95–97, 92–94; 260/486 R

[56] References Cited

U.S. PATENT DOCUMENTS

| 2,377,952 | 6/1945 | Marks | 260/486 R |
| 3,420,751 | 1/1969 | Houghland et al. | 203/83 |
| 3,821,286 | 6/1974 | Pai et al. | 260/486 R |

FOREIGN PATENT DOCUMENTS

| 842,025 | 7/1960 | United Kingdom | 260/486 |
| 1,256,288 | 12/1971 | United Kingdom | 260/486 |

Primary Examiner—Wilbur L. Bascomb, Jr.
Attorney, Agent, or Firm—Frank J. Jordan

[57] ABSTRACT

A process for preparing a purified methacrylic acid ester from a crude methacrylic acid ester containing an isobutyric acid ester as an impurity, comprising the steps of azeotropically distilling the crude methacrylic acid ester in the presence of water to separate as the top distillate the isobutyric acid ester and water together with a small amount of the methacrylic acid ester and recover as the bottoms the greater part thereof, separating the distillate into aqueous and organic phases and further azeotropically distilling the separating organic phase in the presence of water to separate as the distillate the isobutyric acid ester and water together with a very small amount of the methacrylic acid ester and recover as the bottoms the remainder thereof, thereby obtaining the purified methacrylic acid ester.

11 Claims, 1 Drawing Figure

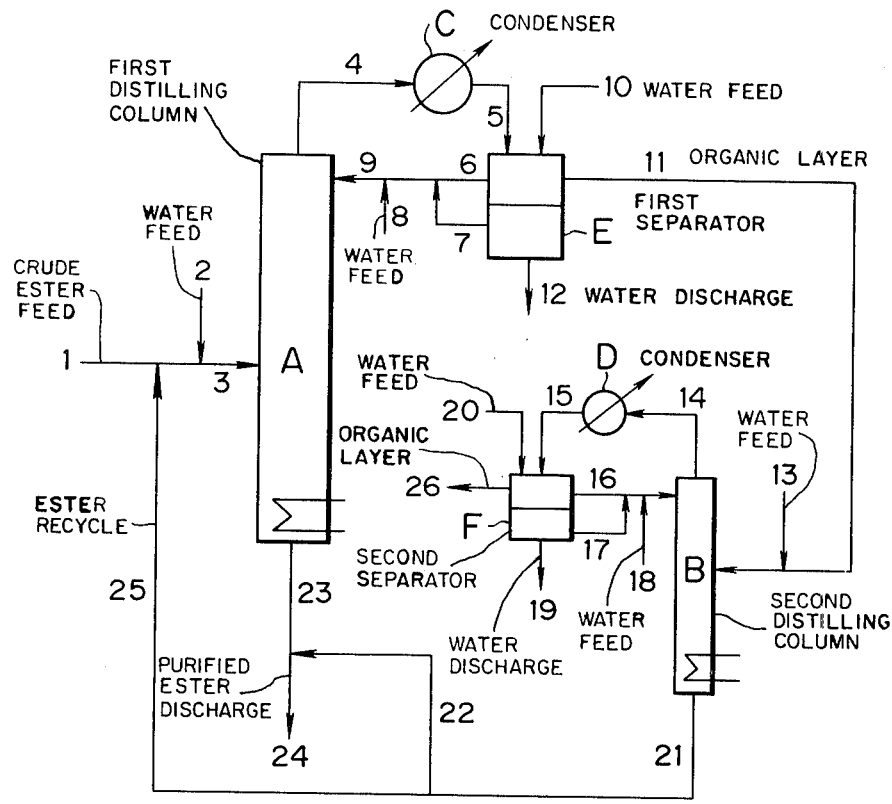

PROCESS FOR PREPARING A PURIFIED METHACRYLIC ACID ESTER

This invention relates to a process for preparing a purified methacrylate from a crude methacrylate containing an isobutyrate as an impurity.

Methacrylates or methacrylic acid esters such as $C_{1-4}$ lower alkyl esters of methacrylic acid are of great commercial importance due to their usefulness in a wide variety of applications. Since they are able to polymerize quite readily, they find one of their principal uses in the preparation of homopolymers thereof and copolymers thereof with other various polymerizable compounds. For example, the homopolymers, particularly methyl methacrylate polymers, find use in many applications because of their capability of being easily molded or cast into shapes, their high degree of clarity, light weight and excellent strength.

Conventional processes for the preparation of methacrylic acid esters include (i) an Acetone Cyanohydrin process, (ii) an Isobutylene Oxidation process, (iii) a tertiary-Butanol Oxidation process, (iv) a Direct Esterification process, (v) an α-hydroxy-isobutyrate Dehydration process and (vi) an Isobutyrate Dehydrogenation or Methoxyisobutyrate Demethylation process (see, for example, Kirk-Othmer, ENCYCLOPEDIA OF CHEMICAL TECHNOLOGY, vol. 13, pp. 333-389).

The Isobutylene Oxidation process comprises catalytically oxidizing isobutylene or a $C_4$ hydrocarbon fraction containing isobutylene with oxygen, air or nitric acid to methacrylic acid or methacrolein which is further oxidized to methacrylic acid, and then esterifying the thus-obtained methacrylic acid with an alcohol thereby producing a methacrylic acid ester. The tertiary-Butanol Oxidation process is carried out in the same manner as the Isobutylene Oxidation process except that the t.-butanol is catalytically oxidized to methacrolein. The Direct Esterification process comprises esterifying, for example, methacrylic acid with an alcohol. The crude methacrylic acid esters as produced by these conventional processes contain various impurities which include the unreacted alcohol, water produced by the esterification, and unreacted methacrylic acid, as well as by-products such as methyl ether, ketones, fatty acids, isobutyrates (isobutyric acid esters) and other fatty acid esters and polymerized materials. It was an important problem to those in the art to obtain a purified methacrylic acid ester by removing from the crude methacrylic acid ester the isobutyric acid ester which is among said impurities and produced as one of the by-products. The reason for said removal is that if, for example, methyl methacrylate containing methyl isobutyrate therein is subjected to polymerization then the methyl isobutyrate, which is a saturated compound, will still remain in the resulting methyl methacrylate polymer without participation in the polymerizing reaction, and that even if the methyl isobutyrate so remaining is very small in amount it will constitute a very undesirable contamination because of its offensive odor. It is therefore necessary to remove the methyl isobutyrate completely.

It should be noted that a methacrylic acid ester and the corresponding isobutyric acid ester referred to throughout this spcification are represented respectively by the following formulae (1) and (2):

and

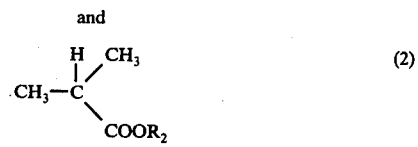

wherein $R_1$ and $R_2$ are identical with each other and they may each be alkyl preferably having 1 - 4 carbon atoms.

As previously mentioned, the thorough removal of the methyl isobutyrate is necessary; however, it is difficult to separate methyl isobutyrate from a crude methacrylic acid ester (which means a mixture of a methacrylic acid ester and the corresponding isobutyric acid ester). This is because the methacrylic acid ester is structurally different from the corresponding isobutyric acid ester only in that the former has a double bond or ethylenic unsaturation while the latter does not, whereby they are not so substantially differentiated from each other in various properties such as boiling point, vapor pressure, solubility in water, and azeotropic formation (including compounds with which they form an azeotropic mixture, composition of the azeotropic mixture, and azeotropic temperature) as to enable them to be readily separated from each other.

The following Table 1 illustrates, for comparison, typical methacrylic acid esters and the corresponding typical isobutyric acid esters as to the respective boiling points of the esters, the respective boiling points of azeotropic mixtures thereof with water or methanol (at atmospheric pressure), and the respective compositions of the azeotropic mixtures.

Table 1

| Ester | B. P. of ester (° C) | Azeotropic mixture with water | | Azeotropic mixture with methanol | |
|---|---|---|---|---|---|
| | | B. P. (° C) | Composition* | B. P. (° C) | Composition* |
| Methacrylic acid methyl ester | 100.3 | 83 | 86 | 64.2 | 15.5 |
| Isobutyric acid methyl ester | 92.3 | 77.7 | 93.2 | 64.0 | 25 |
| Methacrylic acid ethyl ester | 118.9 | 88.2 | 76.3 | — | — |
| Isobutyric acid ethyl ester | 110.1 | 85.2 | 84.8 | — | — |
| Methacrylic acid propyl ester | 141 | 94.4 | 61.8 | — | — |
| Isobutyric acid propyl ester | 133.9 | 92.2 | 69.2 | — | — |

Since, as is clear from Table 1, the boiling point of each of the methacrylic acid esters is close to that of the corresponding isobutyric acid ester, it would require a fractionation at a high reflux ratio by the use of a highly multi-plate fractionating column to separate a mixture of the methacrylic acid ester and the corresponding isobutyric acid ester into the two component esters only by distillation; in the case of such severe fractionation polymerized materials will be produced due to a rise in the bottom temperature of the column. Therefore, the severe fractionation as mentioned above is very disadvantageous to effect on an industrial scale in view of its poor economy and operational manner. Indeed, there have heretofore been proposed neither processes for the removal of isobutyric acid esters only by conventional distillation nor satisfactory processes for the removal of isobutyric acid esters by azeotropic or extractive distillation or the like. In azeotropic distillation a suitable selective azeotrope former must be employed. However, as is evident from the data such as the boiling points of the azeotropic mixtures of the methacrylate or isobutyrate with water or methanol, it appeared very difficult to find a suitable selective azeotrope former which selectively forms a desired azeotrope with an isobutyric acid ester. In other words, it was surmised that an azeotrope former which forms an azeotrope with an isobutyric acid ester would also form an azeotrope with a methacrylic acid ester and that the two azeotropes would be close to each other in azeotropic composition and boiling point and the like. As far as is known up to the present, there have been proposed no processes for removing isobutyric acid esters by azeotropic distillation with an azeotrope former therefor.

In addition, it is difficult to select a solvent which is suitable for use in the extractive distillation of an isobutyric acid ester and, as far as is known until the present, there have been known no solvents which are suitable for use in an extractive distillation for removing an isobutyric acid ester from a crude methacrylic acid ester. As mentioned before, it is difficult to remove the corresponding isobutyric acid ester readily from the crude methacrylic acid ester thereby obtaining the methacrylic acid ester in a purified form. A process for the effective removal of the isobutyric acid ester has thus been sought.

A primary object of this invention is to provide a process for preparing a purified methacrylic acid ester which comprises removing a corresponding isobutyric acid ester from a crude methacrylic acid ester in an efficient, economical and operationally satisfactory manner.

This object is achieved by distilling a crude methacrylic acid ester in the presence of water to obtain a distillate, separating the thus obtained distillate into an organic phase and an aqueous phase and then distilling the organic phase in the presence of water; more particularly, the object is attained by (I) distilling the crude methacrylic acid ester in the presence of water to obtain a distillate consisting substantially of the corresponding isobutyric acid ester and water which are accompanied by part of the methacrylic acid ester and to recover as the bottoms a first purified methacrylic acid ester, (II) separating the thus obtained distillate into an aqueous phase and an organic phase consisting substantially of the isobutyric and methacrylic acid esters so distilled off and then (III) distilling the thus separated organic phase in the presence of water to distill off the corresponding isobutyric acid ester and water, accompanied by a very small amount of the methacrylic acid ester and simultaneously recover a second purified methacrylic acid ester as the bottoms.

This invention will be further detailed hereinbelow.

The conventional crude methacrylic acid ester to be purified, originally contains water in not a few cases. For example, the water is produced by the esterification reaction for obtaining the crude methacrylic acid ester, or it is carried into the crude ester when the unreacted alcohol is separated from the esterification reaction products using water as a solvent for the alcohol in a liquid-liquid extracting step.

The water accompanying, or contained in, the crude methacrylic acid ester forms an azeotrope respectively with the methacrylic acid ester and the corresponding isobutyric acid ester, and the difference in boiling points between the two azeotropes so formed is smaller than that between those of the original methacrylic and isobutyric acid esters as listed in Table 1. This indicates that the presence of water in the crude methacrylic acid ester makes complicated or harder the separation of the corresponding isobutyric acid ester from the methacrylic acid ester. In other words, if it is attempted to separate the isobutyric acid ester from the methacrylic acid ester only by the use of conventional distillation without consideration of economy then it would be necessary to remove the water from the crude methacrylic acid ester prior to said separation, while even if it is attempted to select an azeotrope former to effect azeotropic distillation therewith for such separation then it would of course be considered unsuitable to use water as the azeotrope former.

The present inventors have made intensive studies in attempts to find a process for effectively removing from a crude methacrylic acid ester a corresponding isobutyric acid ester and, as a result of their studies, they have found that the presence of a suitable amount of water in the crude methacrylic acid ester is extremely preferred to carry out the removal of the corresponding isobutyric acid ester effectively, thus accomplishing the object of this invention.

In the first step of the process of this invention the crude methacrylic acid ester is distilled in the presence of water which may be introduced in the form of steam to the distillation system (this distillation being hereinafter referred to as "first distillation"). In the course of the first distillation substantially the whole of the isobutyric acid ester is distilled off together with the water from the crude methacrylic acid ester. This is because, as is seen from Table 1, the isobutyric acid ester and water form an isobutyric acid ester-water azeotrope having (1) a lower boiling point and (2) a higher ester content than those of a methacrylic acid ester-water azeotrope. In the first distillation part of the methacrylic acid ester is distilled off in the form of an azeotrope with the water while accompanying the isobutyric acid ester-water azeotrope which is being distilled off since the boiling point of the methacrylic acid ester-water azeotrope is higher than, but is close to, that of the isobutyric acid ester-water azeotrope.

Therefore, the more water that is added, the more methacrylic acid ester that is distilled off while accompanying the other ingredients (the corresponding isobutyric acid ester and the water) as mentioned above, in the practice of the first distillation. In view of this, the first distillation according to this invention is carried out in such a manner that water is added to the crude methacrylic acid ester in amounts sufficient to assure the distilling off of substantially the whole of the isobutyric acid ester and the simultaneous distilling off of part of the methacrylic acid ester. The addition of unduly much water is of course undesirable since this will cause the methacrylic acid ester, with which the isobutyric acid ester is accompanied when distilled, to be distilled off in undesirably large amounts. Thus, the amount of water added to the crude methacrylic acid ester should be such that substantially the whole of the isobutyric acid ester is distilled off and, at the same time, the amount of the methacrylic acid ester distilled off is minimized.

In the practice of the first distillation, a purified methacrylic acid ester containing substantially no corresponding isobutyric acid ester is obtained as the bottoms from the bottom of a distillation column for the first distillation, while there is obtained as the distillate from the top of the column substantially the whole of the corresponding isobutyric acid ester previously contained in the crude methacrylic acid ester, substantially the whole of the water previously added and part of the methacrylic acid ester originally present in the crude methacrylic acid ester. If the methacrylic acid ester contained in the distillate can be considered to be an acceptable loss from the view-point of economy then the first distillation alone would be enough to obtain a purified methacrylic acid ester with the acceptable loss from the crude methacrylic acid ester. In reality, however, the amount of the methacrylic acid ester contained in the distillate is not so small as may be neglected. It is thus necessary to recover from the distillate the methacrylic acid ester in such an amount that the amount of this ester lost without being recovered is economically negligible.

Thus, in the process of this invention, there is included a second step wherein said distillate is separated into an organic phase consisting substantially of the corresponding isobutyric acid ester and the methacrylic acid ester and an aqueous phase containing substantially none of the two acid esters, and there is further included a third step wherein the organic phase is distilled in the presence of a suitable amount of water thereby to recover as the distillate the water, substantially the whole of the isobutyric acid ester and an economically negligible amount of the methacrylic acid ester with which said water and isobutyric acid ester are accompanied when distilled and also to recover as the bottoms a purified methacrylic acid ester freed of the isobutyric acid ester (the distillation effected in the third step being hereinafter referred to as "second distillation").

The second and third steps will be detailed hereinbelow.

The distillate obtained by the first distillation may be deemed to be a mixture of an isobutyric acid ester-water azeotrope and a methacrylic acid ester-water azeotrope. If, thus, the distillate obtained by the first distillation should be subjected to the second distillation in the third step without being subjected to the treatment of the second step before attempting to separate said two azeotropes from each other then it would undoubtedly require the use of a high multi-plate distillation column (having a large number of plates therein) and a distillation operated at a very high reflux ratio to attain a satisfactory separation in view of the differences in boiling point between said two azeotropes as indicated in Table 1; in this case, unless the distillation conditions used, such as the reflux ratio and number of plates of a distilling column, are severer than those for the first distillation then a distillate to be obtained as the distillate by the second distillation will be one which is substantially not different from the feed, that is the distillate obtained by the first distillation. The reason for this is that the distillate obtained by the first distillation contains water in amounts enough to form an azeotrope of the water and substantially the whole of each of the coexistent isobutyric and methacrylic acid esters. It is therefore possible to remarkably decrease the amount of the methacrylic acid ester distilled in the form of an azeotrope with water in the practice of the second distillation by previously removing the water in some manner from the distillate obtained by the first distillation.

Now, it is a very great convenience that the greater part of the moisture in the distillate from the first distillation forms an aqueous phase after being cooled and condensed, thereby usually separating itself easily from the coexistent isobutyric and methacrylic acid esters. This is apparent from the fact that the water contents of the azeotropes are very high as compared with the solubilities in the esters.

Thus, the distillate from the first distillation is introduced to the second step where it is separated into an organic phase which is an upper layer consisting substantially of the corresponding isobutyric acid ester and the methacrylic acid ester, and an aqueous phase which is a lower layer substantially free of the two acid esters. The organic phase so separated is then introduced to the third step where it is subjected to the second distillation in the presence of a suitable amount of water (the water being allowed to be introduced in the form of steam) thereby to recover substantially the whole of the isobutyric acid ester and the water as the distillate from the top of the distilling column and also to recover a purified methacrylic acid ester free of the isobutyric acid ester as the bottoms from the bottom of the column.

The separation treatment in the second step makes it possible to remove from the system the greater part of the water present in the distillate in amounts enough to form an azeotrope of the water and substantially the whole of the methacrylic acid ester, thereby facilitating the recovery of the methacrylic acid ester by the second distillation in the third step. The second step is thus an indispensable one in the process of this invention.

When carrying out the second distillation in the third step, the isobutyric acid ester and water are distilled off while being accompanied with part of the methacrylic acid ester, as in the case of the first distillation; however, the amount of the methacrylic acid ester so distilled off by the second distillation is extremely small as compared with the amount of the methacrylic acid ester distilled off by the first distillation, the extremely small amount being usually negligible as a loss. The amount of water added for the second distillation as in the case of the first distillation, should be such that the distilling off of substantially the whole of the isobutyric acid ester in the organic phase is assured and the amount of the methacrylic acid ester therein distilled off is preferably minimized.

According to this invention, it is essential not only to carry out said first, second and third steps in combination and in that order but also to effect the first and second distillations in the presence of respectively suitable amounts of water. In said distillations, the use of water in unsuitably small amounts will result in an insufficient removal of the corresponding isobutyric acid ester as the impurity, whereas the use of water in unsuitably large amounts will result in an increase in loss of the methacrylic acid ester since in this case comparatively much of the methacrylic acid ester will be distilled simultaneously with the distillation of the other ingredients (the isobutyric acid ester, water, etc.). In view of these disadvantages, suitable amounts of water used in said distillations should preferably be determined by the amount of the isobutyric acid ester contained in the crude methacrylic acid ester. For example, the crude methacrylic acid ester obtained by the previously mentioned Isobutylene Oxidation process usually contains the isobutyric acid ester in amounts of about 0.1 – about 3% by weight of the crude ester; the amounts of water added to the original crude methacrylic acid ester and the organic phase should preferably be 0.2 – 5% for the first distillation and 0.2 – 10% for the second distillation, based on the weight of the original crude ester and the organic phase, respectively, in order to attain a substantially perfect removal of the isobutyric acid ester and simultaneously minimize the loss of the methacrylic acid ester.

In the first distillation, the crude methacrylic acid ester is distilled after the addition of water thereto to assure a water content suitable for the distillation; however, if the original crude methacrylic acid ester contains suitable amounts of water which have been introduced thereinto during the production thereof then the crude ester may be fed to the distilling column without externally supplying water thereto.

Since the distillate obtained by the first distillation contains water in greater amounts than are soluble in the whole of the methacrylic and corresponding isobutyric acid esters contained in the distillate, organic and aqueous phases usually form after the condensation thereof. Further amounts of water may be incorporated as required to promote the subsequent separation into organic and aqueous phases in the second step.

The organic phase or layer from the second step contains, in many cases, water in desired amounts due to the contact of this phase with the aqueous phase in the second step, and it may generally be subjected, as it is, to the second distillation in the third step. If the purified methacrylic acid ester recovered as the bottoms by the second distillation contains the corresponding isobutyric acid ester in unacceptably large amounts then the bottoms are preferably recycled to the distilling column for the first distillation in order to distil off the remaining isobutyric acid ester, while if it contains substantially no isobutyric acid ester then it may be combined with the purified methacrylic acid ester recovered as the bottoms from the first distillation.

In addition, the distillate from the second distillation will usually form organic and aqueous phases after the condensation thereof in the same manner as the distillate from the first distillation and, if the organic phase so formed is considered to contain the methacrylic acid ester in too high amounts to be discarded then the distillate from the second distillation may, as required, be treated in a fourth step for separation into organic and aqueous phases as in the second step and then in a fifth step wherein a third distillation is effected for the recovery of the methacrylic acid ester by distillation as in the third step. However, it is usually sufficient to employ the first distillation as the first step, the first phase separation as the second step and the second distillation as the third step to accomplish the purification of the crude methacrylic acid ester according to this invention, the purification meaning to remove from the crude methacrylic acid ester substantially the whole of the corresponding isobutyric acid ester with a minimum or economically acceptable small loss of the methacrylic acid ester thereby obtaining a purified methacrylic acid ester.

By way of an illustration, there will hereinbelow be calculated how much of a methacrylic acid ester is finally lost to obtain a purified methacrylic acid ester from a crude methacrylic acid ester by the use of the process of this invention. In this calculation, the presence of the corresponding isobutyric acid ester is neglected.

Assuming that 100 parts by weight of the crude methacrylic acid methyl ester (methyl methacrylate) are subjected to the first distillation in the presence of 1.5 parts by weight of water, the resulting distillate will contain about 9 parts of the ester (the amount of the ester distilled in the form of an azeotrope with water being considered to be about 6 times that of the water, that is about 9 parts by weight) and about 1.5 parts by weight of water. Further assuming that about two % by weight of water is dissolved in the organic phase or layer after condensation in the second step, the water retained in the organic phase will be about 0.18 parts in amount and the remaining water (about 1.32 parts) will be withdrawn from the system. Thus, a distillate obtained by the second distillation will contain an azeotropic mixture of 0.18 parts of water and about 1.08 parts by weight of the methyl methacrylate. The amount of this methyl methacrylate in said distillate is about 1.08%, which is an extremely small amount, based on the weight of the original crude methyl methacrylate fed to the distilling column and, therefore, it may be deemed to be a negligible loss thereof.

The above-mentioned calculation is a rough one for estimating the loss of the desired ester, and the actual result may somewhat vary depending on the content of the corresponding isobutyric acid ester, operational conditions for distillation, amount of water added, and the like. If a satisfactory result is not obtained by the second distillation, then the methacrylic acid ester will further be recovered by the third distillation if necessary. The results or effects obtained by the third distillation can easily be inferred from the above illustrative calculation.

Furthermore, the advantages of an apparatus for carrying out the process of this invention will hereunder be mentioned by reference to numerical values obtained by rough calculation. For example, isobutyric acid methyl ester (methyl isobutyrate) and methacrylic acid methyl ester (methyl methacrylate) are different from each other by only 8° C in boiling point as indicated in Table 1. If a crude methacrylic acid methyl ester containing 1% by weight of isobutyric acid methyl ester is to be purified to an extent that the resulting purified methacrylic acid methyl ester contains not more than 100 ppm of isobutyric acid methyl ester and the resulting loss of methacrylic acid methyl ester is limited to not more than 1%, this will require the use of a distilling column having 90 plates therein and a distilling operation at a reflux ratio (r) of approximately 200 in view of said difference in boiling point of only 8° C.

If, however, such purification is to be effected by the process of this invention then the first distillation, as indicated in Example 1 to be described later, will be operated at a reflux ratio (r) of 4.8, which is about one-fortieth of the stated above ratio, by the use of a distilling column having therein 45 plates which are a half of those of the column referred to above, whereby the amount of reflux is reduced to about one-third and consequently a distilling column having a reduced diameter may be employed with a remarkably decreased operation cost.

The second distillation is effected on the organic phase or layer obtained from the distillate from the first distillation, and the amount of the organic phase treated is greatly decreased as compared with that of the crude methacrylic acid ester fed to the first step for the first distillation (usually being decreased to one-tenth of the amount of the crude methacrylic acid ester). Thus a distilling column for the second distillation may be a small-scale one.

In summary, this invention is preferably applicable to the preparation of a purified methacrylic acid ester from a crude methacrylic acid ester containing a corresponding isobutyric acid ester as the impurity and is more preferably applicable to cases where the methacrylic and isobutyric acid esters are each an alkyl ester having 1 – 4 carbon atoms.

This invention will be explained in more detail by reference to the accompanying drawing.

A crude methacrylic acid ester containing a very small amount of a corresponding isobutyric acid ester, together with part or the whole of the bottoms from a second distilling column B (the bottoms being passed through line 25 to line 1) if necessary, is fed through lines 1 to 3 to a first distilling column A. To the first column A through line 2 is fed part or the whole of water the amount of which is preferably 0.2 – 5% by weight of the crude methacrylic acid ester fed through lines 1 and 3. Such an amount of water may alternatively be fed to the distillation system of the column A through lines 8 or 10 and 9 as required.

The crude methacrylic acid ester so fed is then distilled in the presence of a suitable amount of water thereby to obtain a purified methacrylic acid ester as the bottoms through line 23 from the bottom of the column A and obtain gases as the distillate from the top thereof. The gases are passed through line 4 to a condenser C where they are condensed, and the condensed materials are then introduced into a separator E where they are separated into an organic phase (upper layer) consisting substantially of the isobutyric and methacrylic acid esters, and an aqueous phase (lower layer). In the separator E, low boiling and comparatively water soluble ingredients such as the unreacted alcohol, may be condensed thereby sometimes hindering the separation from proceeding efficiently. In such troublesome cases, water may be fed through line 10 to the separator to promote the separation, and part or the whole of the water so fed may be added to a reflux stream returning to the column A through lines 7 and 9, thus constituting part or the whole of the water necessary to be added to the crude methacrylic acid ester in the column A.

An excess of water of the aqueous layer in the separator E is discharged through line 12 and is, if necessary, passed to a unit for the recovery of the solute of the aqueous layer therefrom or a unit for the disposal thereof. On the other hand, the organic layer or phase is partly passed, for reflux, through lines 6 and 9 to the column A while the remainder thereof is passed through line 11 to a second distilling column B.

The organic phase passed to the second column B contains a small amount of water since it previously was in contact with the water in the separator E and, if necessary, it may be mixed with water introduced through lines 13 and/or 18 and 20. The extent of the introduction of water is determined in view of the degree of separation between the aqueous and organic phases in the separator E, the content of the corresponding isobutyric acid ester, the operational conditions of the second column B, and the like.

The gaseous distillate consisting substantially of the isobutyric acid ester, water and a very small amount of the methacrylic acid ester each in the gaseous form, obtained from the top of the second column B is passed through line 14 to a condenser D where it is condensed. The condensed mass is then passed to a separator F where it is, if necessary, mixed with water introduced via line 20 to promote the separation thereof into an aqueous phase (lower layer) and an organic phase (upper layer).

The aqueous and organic phases are partly returned, as refluxes, through lines 17 and 16 to the second column B, respectively, while the remainder of the aqueous phase is withdrawn through line 19 for disposal or recovery of the solute in the remainder as in the case of the aqueous phase discharged through line 12. The remainder of the organic phase, on the other hand, is withdrawn through line 26 to a third distilling column C (not shown) for further recovery of the methacrylic acid ester from the remainder, to a step for recovery of the isobutyric acid ester therefrom or to a step for disposal thereof.

The bottoms (the methacrylic acid ester) from the second column B is passed through lines 21 and 22 to combine with the bottoms passed through line 23 from the first column A. If necessary, the bottoms or the methacrylic acid ester so combined may be subjected to a further purification treatment such as the removal of higher boiling ingredients which might be contained in said combined ester, to obtain a further purified methacrylic acid ester or else they may partly or wholly be returned through lines 21 and 25 to the first column A for enhancing the efficiency of removal of the isobutyric acid ester.

In connection with this, Japanese Pat. Gazettes Nos. 1370/73 and 36603/71 disclose processes comprising distilling a crude methacrylic acid ester by the use of a distilling column to recover a distillate, separating the thus recovered distillate into an organic phase and an aqueous phase into which the impurities have been transferred from the distillate, and then recycling the organic phase to the distilling column. These known processes are very useful in the removal of impurities (such as acetone and methanol) which are much more highly water-soluble than the methacrylic acid ester and are easily transferable to the aqueous phase by washing the distillate from the distilling column with water. Since, however, the isobutyric acid ester to be removed is less soluble in water than is the methacrylic acid ester (Examples of solubility in water at 20° C : 1.59% by weight for methacrylic acid methyl ester, and 0.95% by weight for isobutyric acid methyl ester), it is difficult to effect the selective removal of the isobutyric acid ester by extraction with water.

Even if, thus, the organic phase containing the corresponding isobutyric acid ester to be removed is recycled to the distilling column, substantially the whole of the isobutyric acid ester will be transferred into the methacrylic acid ester at the bottom of the column. The isobutyric acid ester is therefore impossible to remove by the use of the processes disclosed in the above-mentioned Japanese Patent Gazettes.

In the practice of this invention, on the other hand, the organic phase of the distillate from the first distilling column is distilled in the second distilling column to remove the corresponding isobutyric acid ester from the system while inhibiting the loss of the methacrylic acid ester to a minimum, thereby recovering the methacrylic acid ester which is recycled to the first distilling column if desired. The economical and technical effects or advantages obtained by the practice of this invention are as previously mentioned.

This invention will be further detailed by reference to the Examples in which all percentages and ppm are by weight unless otherwise specified.

EXAMPLE 1

A crude methacrylic acid prepared by the Isobutylene Oxidation process is esterified to obtain a crude methacrylic acid methyl ester containing a small amount of an isobutyric acid methyl ester and methanol. The crude methacrylic acid methyl ester so obtained is incorporated with water to prepare a mixture of a crude methacrylic acid methyl ester consisting substantially of 94.60% methacrylic acid methyl ester, 0.90% isobutyric acid methyl ester, 2.05% methanol, 1.60% water and the balance being methacrylic acid and a very small amount of high boiling material. This crude methyl ester so prepared is incorporated with 0.05% hydroquinone to form a mixture which is then fed at a flow rate of 37.50 kg/hr to a first distilling column (column diameter, 10 inch; 45 bubble cap plates; feed supplied at 15th plate from the top) where it is distilled at a reflux ratio of 4.8 and at atmospheric pressure. The temperatures of the top and bottom of the distilling column are, on the average, 84.3° C and 106.5° C, respectively.

Since the distillate after condensation tends to take some time to separate into two layers, 5.67 kg/hr of about 33 kg/hr of the distillate are mixed with 0.31 times it weight of water and then separated into upper and lower layers and, on the other hand, the remaining distillate (about 27 kg/hr) is returned, after being mixed with 0.02% hydroquinone, as the reflux to the first distilling column.

The upper layer (organic phase) consists of 1.92% methanol 7.51% isobutyric acid methyl ester, 89.12% methacrylic acid methyl ester and 1.45% water; and the amount of the organic phase corresponds to 4.42 kg/hr.

The bottoms withdrawn at 31.82 kg/hr from the bottom of the first column are found to contain 98.99 % methacrylic acid methyl ester and about 60 ppm of isobutyric acid methyl ester.

The organic phase (the crude methacrylic acid methyl ester which contains 1.45% water) is fed at a feed rate of 6.20 kg/hr to a second distilling column (column diameter, 12.5 mm $\phi$; portion of column filled with McMahon packing (saddle type ring), 3 m along the height of column; location of feed inlet of column, 1m downward from the top of the packing-filled portion) operated under atmospheric pressure where it is distilled at a reflux ratio of 5.10. The distillate obtained at 1.07 kg/hr is mixed with water in an amount (by weight) 0.28 times as large as the distillate and then separated into two layers. The organic layer (0.89 kg/hr) so separated consists of 52.05% isobutyric acid methyl ester, 44.64% methacrylic acid methyl ester and the balance being methanol and water.

The bottoms (5.13 kg/hr) recovered from the bottom of the second distilling column contain about 270 ppm of isobutyric acid methyl ester and methacrylic acid methyl ester of at least 99% purity. Said bottoms are mixed with those from the first column and the resulting mixture is freed of high boiling material contained therein obtaining a purified methacrylic acid methyl ester having an analysis of 99.5% methacrylic acid methyl ester, about 120 ppm of water and about 80 ppm of isobutyric acid methyl ester.

The over-all yield of the purified methacrylic acid methyl ester to the methacrylic acid methyl ester in relation contained in the crude methacrylic acid methyl ester fed to the first distilling column is 98.94%.

COMPARATIVE EXAMPLE

There is prepared a crude methacrylic acid ester having approximately the same composition as the crude one fed to the distilling column in Example 1. This crude methacrylic acid methyl ester consists substantially of 2.30% methanol, 0.93% isobutyric acid methyl ester, 95.82% methacrylic acid methyl ester, 0.90% methacrylic acid and 300 ppm water (this amount of water is one to which the original higher water content has been decreased with the greatest effort). The crude methyl ester is incorporated with 0.1% hydroquinone to form a mixture which is then fed at 26.90 kg/hr to the first distilling column (as in Example 1) where it is distilled at a reflux ratio of 50 or 100, the reflux ratio being about 10 or 20 times as high as that in Example 1. The result is that the content of isobutyric acid methyl ester in the bottoms recovered from the bottom of the column is 0.49% for a reflux ratio of 50 and 0.25% for a reflux ratio of 100. As mentioned above, isobutyric acid methyl ester remains in the bottoms in greater amounts in this Comparative example than in Example 1, thus rendering it impossible to attain such an effective removal that the amount of isobutyric acid methyl ester remaining in the bottoms is decreased to not more than 100 ppm as in Example 1.

EXAMPLE 2

Methacrylic acid ethyl ester containing isobutyric acid ethyl ester and ethanol is mixed with a small amount of water to prepare a crude methacrylic acid ethyl ester. The crude ethyl ester containing 3.20% ethanol, 0.40% isobutyric acid ethyl ester, 1.05% water, 94.65% methacrylic acid ethyl ester and 0.70% methacrylic acid, is fed at a feed rate of 3.08 kg/hr to the first distilling column (column diameter, 12.5 mm $\phi$; portion of column filled with McMahon packing, 3 m along the height of column; location of feed inlet of column, 1 m downward from the top of the packing-filled portion) operated at a reflux ratio of 7.0 in order to distil the crude ethyl ester. The resulting distillate is removed at 257 g/hr from the column, and the distillate so sampled is incorporated with water in an amount 1.2 times that of the distillate to effect the separation of the distillate into two layers. As one of the two layers, there is thus obtained an organic layer containing 2.88% ethanol, 9.11% isobutyric acid ethyl ester, 1.44% water and 86.57% methacrylic acid ethyl ester, at a rate of 132 g/hr.

On the other hand, the analysis of the bottoms from the distilling column indicates that 99.23% methacrylic acid ethyl ester is present and about 70 ppm of isobutyric acid ethyl ester remains in the bottoms.

The aforesaid organic layer obtained by water washing the distillate from the first distilling column is about one kg in all, and it is batchwise distilled to recover as the bottoms about 0.85 kg of methacrylic acid ethyl ester containing 760 ppm of isobutyric acid ethyl ester. The bottoms so recovered are combined with the bottoms from the first distilling column, and the whole mass is distilled at a reduced pressure of 400 mm Hg Absolute to obtain a purified methacrylic acid ethyl ester containing 100 ppm of isobutyric acid ethyl ester. The purified methacrylic acid ethyl ester is 99.7% in purity and obtained in an overall yield of 95.0%.

What is claimed is:

1. A process for preparing a purified methacrylic acid ester from a crude methacrylic acid ester containing an isobutyric acid ester as an impurity which comprises the steps of:
   1. firstly distilling said crude methacrylic acid ester in the presence of water to separate as the distillate the isobutyric acid ester and water together with part of the methacrylic acid ester and recover as the bottoms a first purified methacrylic acid ester,
   2. separating said distillate into an aqueous phase and an organic phase consisting substantially of the isobutyric acid ester and the methacrylic acid ester, and
   3. secondly distilling the thus separated organic phase in the presence of water to separate as the distillate the isobutyric acid ester and water together with a very small amount of the methacrylic acid ester and recover as the bottoms a second purified methacrylic acid ester, thereby obtaining the purified methacrylic acid ester, wherein the water is present in each of the steps (1) and (3) in such amounts that substantially the whole of the isobutyric acid ester contained in the crude methacrylic acid ester is distilled off while minimizing the amount of the methacrylic acid ester distilled off.

2. A process as claimed in claim 1, wherein when the crude methacrylic acid ester to be distilled in the step (1) contains the isobutyric acid ester in an amount of 0.1 - 3% by weight thereof, water is added to the crude methacrylic acid ester in the step (1) in an amount of 0.2 - 5% by weight of the crude acid ester and water is added to the organic phase in the step (3) in amounts of 0.2 - 10% by weight of the organic phase.

3. A process as claimed in claim 1, wherein the distillation in each of the steps (1) and (3) is carried out at atmospheric pressure.

4. A process as claimed in claim 1, wherein the water necessary for the first distillation is added to the crude methacrylic acid ester in the step (1) prior to the first distillation.

5. A process as claimed in claim 1, wherein the water necessary for the second distillation is added to the separated organic phase in the step (3) prior to the second distillation.

6. A process as claimed in claim 1, wherein the methacrylic and isobutyric acid esters are each an alkyl ester wherein the alkyl contains 1 - 4 carbon atoms.

7. A process as claimed in claim 7, wherein the alkyl is methyl.

8. A process as claimed in claim 1, wherein the crude methacrylic acid ester is one obtained by an Isobutylene Oxidation process.

9. A process as claimed in claim 1, wherein the crude methacrylic acid ester is one obtained by a tertiary-Butanol Oxidation process.

10. A process as claimed in claim 1, wherein the crude methacrylic acid ester is one obtained by a Direct Esterification process.

11. A process as claimed in claim 1, wherein the crude methacrylic acid ester is one obtained by an Acetone Cyanohydrin process.

* * * * *